United States Patent
Nakamura et al.

(10) Patent No.: US 7,928,247 B2
(45) Date of Patent: Apr. 19, 2011

(54) POLYMERIZABLE COMPOSITION, RESIN USING THE SAME, OPTICAL COMPONENT AND COMPOUND

(75) Inventors: Mitsuo Nakamura, Chosei-gun (JP); Shinichi Usugi, Chiba (JP); Hiroshi Naruse, Ichihara (JP); Atsuo Otsuji, Chiba (JP)

(73) Assignee: Mitsui Chemicals, Inc., Minato-Ku, Tokyo (JP)

( * ) Notice: Subject to any disclaimer, the term of this patent is extended or adjusted under 35 U.S.C. 154(b) by 162 days.

(21) Appl. No.: 12/305,536

(22) PCT Filed: Jun. 14, 2007

(86) PCT No.: PCT/JP2007/000633
§ 371 (c)(1),
(2), (4) Date: Dec. 18, 2008

(87) PCT Pub. No.: WO2007/148432
PCT Pub. Date: Dec. 27, 2007

(65) Prior Publication Data
US 2009/0192288 A1    Jul. 30, 2009

(30) Foreign Application Priority Data

Jun. 21, 2006 (JP) ................ 2006-171725
Jun. 21, 2006 (JP) ................ 2006-171730

(51) Int. Cl.
*C07D 327/00* (2006.01)
(52) U.S. Cl. .......................... 549/5; 528/380
(58) Field of Classification Search ............... 528/375, 528/380; 549/5
See application file for complete search history.

(56) References Cited

U.S. PATENT DOCUMENTS

| 3,071,594 A | 1/1963 | Enders et al. |
| 3,169,974 A | 2/1965 | Kohn |
| 3,197,407 A * | 7/1965 | Cyba ........................ 508/299 |
| 2005/0215757 A1 | 9/2005 | Kobayashi et al. |

FOREIGN PATENT DOCUMENTS

| EP | 1 731 547 A1 | 12/2006 |
| JP | 59-187094 A | 10/1984 |
| JP | 9-110979 A | 4/1997 |
| JP | 11-140046 A | 5/1999 |
| JP | 11-322930 A | 11/1999 |
| JP | 2003-327583 A | 11/2003 |
| JP | 2004-310001 A | 11/2004 |
| JP | 2006-169190 A | 6/2006 |
| WO | WO 2005/095490 A1 | 10/2005 |

OTHER PUBLICATIONS

Form PCT/ISA/210 (International Search Report) dated Aug. 14, 2007.

* cited by examiner

*Primary Examiner* — Randy Gulakowski
*Assistant Examiner* — Shane Fang
(74) *Attorney, Agent, or Firm* — Buchanan Ingersoll & Rooney PC

(57) ABSTRACT

Disclosed is a polymerizable composition containing a compound represented by the following general formula (1),

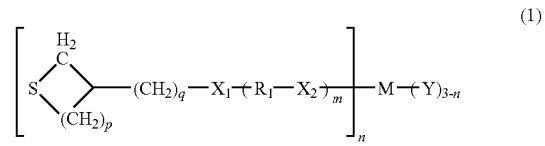

wherein, in the formula, M represents P, P=O or P=S; $X_1$ and $X_2$ each independently represent a sulfur atom or an oxygen atom; $R_1$ represents a divalent organic group; m represents 0 or an integer of not less than 1; n represents an integer of not less than 1 but not more than 3; p and q represent (1, 0) or (0, 1); and Y represents an inorganic or organic residue.

18 Claims, No Drawings

POLYMERIZABLE COMPOSITION, RESIN USING THE SAME, OPTICAL COMPONENT AND COMPOUND

TECHNICAL FIELD

The present invention relates to a polymerizable compound which is useful as a raw material monomer for a transparent resin having a high refractive index, has a cyclic structure containing S (sulfur) in a molecule, and contains a P (phosphorus) atom. More particularly, the invention relates to a polymerizable composition containing the compound, a resin obtained by polymerization of the polymerizable composition, an optical component containing the resin, and the compound.

BACKGROUND ART

Since an inorganic glass has excellent general properties such as excellent transparency and low optical anisotropy, the inorganic glass has been widely used in many fields as a transparent material. However, the inorganic glass has drawbacks such that it is heavy and easily broken, and has bad productivity when producing a product by molding and processing. As a result, a transparent organic polymer material (optical resin) has been used as a material in place of the inorganic glass. As the optical component obtained from such an optical resin, there are, for example, a spectacle lens for vision correction, and a plastic lens such as a camera lens of a digital camera and the like. The optical members have been put to practical use and have come into use. In particular, for the purpose of use in a spectacle lens for vision correction, the organic polymer material is lightweight and hardly broken, and can be dyed for granting great fashionability, as compared to the lens made of an inorganic glass. Making good use of such merits, the organic polymer material has been widely used.

In the past, a crosslinking type resin obtained by casting polymerization of diethylene glycol bisallylcarbonate as an optical resin used for a spectacle lens under heating (hereinafter commonly referred to as a DAC resin) has been put to practical use. The crosslinking type resin has merits such that transparency and heat resistance are excellent, and the chromatic aberration is low. Due to such merits, it has been used the most for a general-purpose plastic spectacle lens for vision correction. However, the central or peripheral thickness (edge thickness) of the plastic lens becomes large because of the low refractive index (nd=1.50). For that reason, there are problems such that wearing comfort and fashionability are worsened and the like. Therefore, a resin for a plastic lens with a high refractive index capable of solving these problems has been demanded and developed accordingly.

In such a trend, highly superior characteristics have been achieved such that polythiourethane comprising a sulfur atom obtained by casting polymerization of a diisocyanate compound with a polythiol compound is excellent in its transparency and impact resistance, while attaining a high refractive index (nd=1.6 to 1.7) and having relatively low chromatic aberration. Such polythiourethane has been used for the purpose of a high-quality plastic spectacle lens for vision correction in which the thickness is thin and its weight is light.

On the other hand, in a trend to pursue an optical resin having a much higher refractive index, there have been proposed several resins such as a transparent resin obtained by polymerization of a compound having an episulfide group in Patent Documents 1 and 2 or a compound having a thietane group in Patent Document 3, a resin obtained by polymerization of a metal-containing compound such as Se or the like in Patent Documents 4, and the like. However, the transparent resin obtained by polymerization of a compound having an episulfide group has a problem in mechanical properties, the compound having a thietane group has a problem in its polymerization ability, and the resin obtained by polymerization of a metal-containing compound such as Se or the like has a problem in safety. So, there have been demanded for further improvements in such resins. In recent years, there has been demanded an optical resin having required general properties (transparency, thermal properties, mechanical properties and the like) as a plastic lens, while attaining a much higher refractive index (nd), for example, exceeding 1.7. The development of such an optical resin has been made. Under these circumstances, a metal-containing thietane compound has been newly found and an optical resin having a high refractive index (nd) of exceeding 1.7 has been proposed in Patent Document 5.

Patent Document 1: Japanese Patent Laid-open No. 1997-110979
Patent Document 2: Japanese Patent Laid-open No. 1999-322930
Patent Document 3: Japanese Patent Laid-open No. 2003-327583
Patent Document 4: Japanese Patent Laid-open No. 1999-140046
Patent Document 5: International Publication Pamphlet No. 2005/095490

DISCLOSURE OF THE INVENTION

The present invention is to provide a polymerizable composition which exhibits a very high refractive index (nd) of exceeding 1.7 while having general properties (transparency, thermal properties, mechanical properties and the like) required for optical components such as plastic lenses or the like. Furthermore, the present invention is to provide a resin obtained by polymerization of the composition, a method for producing the resin and an optical component containing the resin, a lens and a compound.

In order to solve the above problems, the present inventors have conducted an extensive study and as a result, have completed the present invention. That is, the present invention relates to a compound having a cyclic structure containing S (sulfur) in a molecule, and containing a P (phosphorus) atom.

That is, the present invention is specified by the following matters:

[1] a polymerizable composition containing a compound represented by the following general formula (1),

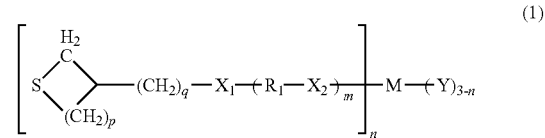

wherein, in the formula, M represents P, P=O or P=S; $X_1$ and $X_2$ each independently represent a sulfur atom or an oxygen atom; $R_1$ represents a divalent organic group; m represents 0 or an integer of not less than 1; n represents an integer of not less than 1 but not more than 3; p and q represent (1, 0) or (0, 1); and Y represents an inorganic or organic residue;

[2] the polymerizable composition as set forth in [1], wherein the general formula (1) is represented by the following general formula (2),

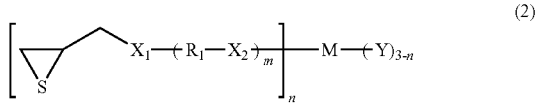

wherein, in the formula, M represents P, P=O or P=S; $X_1$ and $X_2$ each independently represent a sulfur atom or an oxygen atom; $R_1$ represents a divalent organic group; m represents 0 or an integer of not less than 1; n represents an integer of not less than 1 but not more than 3; and Y represents an inorganic or organic residue;

[3] the polymerizable composition as set forth in [2], wherein, in the compound represented by the general formula (2), m is 0;

[4] the polymerizable composition as set forth in [2], wherein, in the compound represented by the general formula (2), m is 0 and $X_1$ is a sulfur atom;

[5] the polymerizable composition as set forth in [2], wherein, in the compound represented by the general formula (2), n is 3, m is 0 and $X_1$ is a sulfur atom;

[6] the polymerizable composition as set forth in [1], wherein the general formula (1) is represented by the following general formula (3),

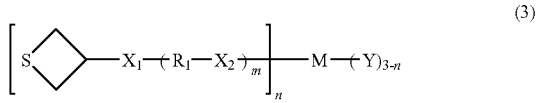

wherein, in the formula, M represents P, P=O or P=S; $X_1$ and $X_2$ each independently represent a sulfur atom or an oxygen atom; $R_1$ represents a divalent organic group; m represents 0 or an integer of not less than 1; n represents an integer of not less than 1 but not more than 3; and Y represents an inorganic or organic residue;

[7] the polymerizable composition as set forth in [6], wherein, in the compound represented by the general formula (3), m is 0;

[8] the polymerizable composition as set forth in [6], wherein, in the compound represented by the general formula (3), m is 0 and $X_1$ is a sulfur atom;

[9] the polymerizable composition as set forth in [6], wherein, in the compound represented by the general formula (3), n is 3, m is 0 and $X_1$ is a sulfur atom;

[10] the polymerizable composition as set forth in [1], further containing a compound represented by the following general formula (7),

[11] a method for producing a resin involving a step of subjecting the polymerizable composition as set forth in any one of [1] to [10] to casting polymerization;

[12] a resin obtained by polymerization of the polymerizable composition as set forth in any one of [1] to [10];

[13] an optical component containing the resin as set forth in [12];

[14] a lens containing the resin as set forth in [12]; and

[15] a compound, wherein, in the compound represented by the general formula (1) as set forth in [1], n is 2 or 3.

The resin obtained by polymerization of the polymerizable composition of the present invention has high transparency, excellent heat resistance and mechanical strength, and has a high refractive index (nd) of exceeding 1.7. Accordingly, the resin is useful as a resin used for an optical component such as a plastic lens or the like.

BEST MODE FOR CARRYING OUT THE INVENTION

The present invention will be described in detail below. Each component will be explained in detail below by using specific examples, but the present invention is not restricted to the following exemplified compounds. Further, in the present invention, the exemplified compounds of each component may be used singly, or a plurality of compounds may be used in combination.

The present invention relates to a compound having a cyclic structure containing S (sulfur) in a molecule, and containing a P (phosphorus) atom. More particularly, the present invention relates to a compound represented by the following general formula (1) and containing a P (phosphorus) atom, and a polymerizable composition containing the compound,

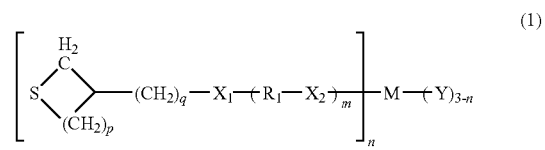

wherein, in the formula, M represents P, P=O or P=S; $X_1$ and $X_2$ each independently represent a sulfur atom or an oxygen atom; $R_1$ represents a divalent organic group; m represents 0 or an integer of not less than 1; n represents an integer of not less than 1 but not more than 3; p and q represent (1, 0) or (0, 1); and Y represents an inorganic or organic residue.

As one of preferred embodiments of the present invention, the compound represented by the above general formula (1) is a compound having one or two or more episulfide groups in a molecule and containing a P (phosphorus) atom. A preferred embodiment of such a compound is a compound wherein M is one or two or more selected from the group consisting of P, P=O or P=S.

Specifically, a compound represented by the general formula (2) can be cited,

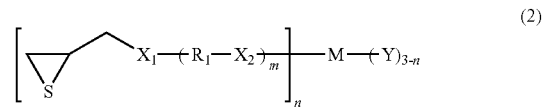

Meanwhile, as another preferred embodiment of the present invention, the compound represented by the above general formula (1) is a compound having one or two or more thietane groups in a molecule and containing a P (phosphorus) atom. A preferred embodiment of such a compound is a compound wherein M is one or two or more selected from the group consisting of P, P=O or P=S.

Specifically, a compound represented by the general formula (3) can be cited,

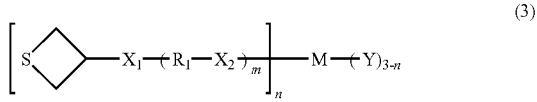

(3)

In the general formulae (1) to (3), M represents P, P=O or P=S.

In the general formulae (1) to (3), $X_1$ and $X_2$ each independently represent a sulfur atom or an oxygen atom. $X_1$ and $X_2$ are each preferably a sulfur atom from the viewpoint of obtaining a high refractive index that is the desired effect of the present invention.

In the general formulae (1) to (3), $R_1$ represents a divalent organic group. Examples of such a divalent organic group include a chained or cyclic aliphatic group, an aromatic group or an aromatic-aliphatic group. In consideration of high refractive index, $R_1$ is preferably a chained aliphatic group having 1 to 20 carbon atoms, a cyclic aliphatic group having 3 to 20 carbon atoms, an aromatic group having 5 to 20 carbon atoms or an aromatic-aliphatic group having 6 to 20 carbon atoms.

More specifically, $R_1$ is preferably a substituted or unsubstituted chained or cyclic aliphatic group having 1 to 20 carbon atoms such as a methylene group, an ethylene group, a 1,2-dichloroethylene group, a trimethylene group, a tetramethylene group, a pentamethylene group, a cyclopentylene group, a hexamethylene group, a cyclohexylene group, a heptamethylene group, an octamethylene group, a nonamethylene group, a decamethylene group, a undecamethylene group, a dodecamethylene group, a tridecamethylene group, a tetradecamethylene group, a pentadecamethylene group and the like; a substituted or unsubstituted aromatic group having 5 to 20 carbon atoms such as a phenylene group, a chlorophenylene group, a naphthylene group, an indenylene group, an anthracenylene group, a fluorenylene group and the like; or a substituted or unsubstituted aromatic-aliphatic group having 6 to 20 carbon atoms such as a —$C_6H_4$—$CH_2$— group, a —$CH_2$—$C_6H_4$—$CH_2$— group, a —$CH_2$—$C_6H_3$(Cl)—$CH_2$— group, a —$C_{10}H_6$—$CH_2$— group, a —$CH_2$—$C_{10}H_6$—$CH_2$— group, a —$CH_2CH_2$—$C_6H_4$—$CH_2CH_2$— group and the like.

$R_1$ is more preferably a substituted or unsubstituted chained or cyclic aliphatic group having 1 to 6 carbon atoms such as a methylene group, an ethylene group, a 1,2-dichloroethylene group, a trimethylene group, a cyclopentylene group, a cyclohexylene group and the like; a substituted or unsubstituted aromatic group having 5 to 15 carbon atoms such as a phenylene group, a chlorophenylene group, a naphthylene group, an indenylene group, an anthracenylene group, a fluorenylene group and the like; or a substituted or unsubstituted aromatic-aliphatic group having 6 to 15 carbon atoms such as a —$C_6H_4$—$CH_2$— group, a —$CH_2$—$C_6H_4$—$CH_2$— group, a —$CH_2$—$C_6H_3$(Cl)—$CH_2$— group, a —$C_{10}H_6$—$CH_2$— group, a —$CH_2$—$C_{10}H_6$—$CH_2$— group, a —$CH_2CH_2$—$C_6H_4$—$CH_2CH_2$— group and the like.

Such a divalent organic group may contain a hetero atom in addition to a carbon atom and a hydrogen atom in the group. As the hetero atom, there can be exemplified an oxygen atom and a sulfur atom. In consideration of high refractive index that is the desired effect of the present invention, the hetero atom is preferably a sulfur atom.

In the general formulae (1) to (3), m represents 0 or an integer of not less than 1. From the viewpoint of high refractive index, m is preferably an integer of 0 to 4, more preferably an integer of 0 to 2 and further preferably an integer of 0 or 1.

In the general formulae (1) to (3), n represents an integer of not less than 1 but not more than 3. n is preferably an integer of 2 or 3 and more preferably an integer of 3 because the mechanical strength is high as the crosslinking density is higher.

In the general formulae (1) to (3), Y represents an inorganic or organic residue. Examples of the residue include a halogen atom, a hydroxyl group, an alkoxy group, an alkylthio group, a phenoxy group, a phenylthio group, an alkyl group, a phenyl group and the like.

Furthermore, in the general formula (1), p and q represent (1, 0) or (0, 1). That is, when any one of p and q is 1, the other one is 0. Herein, when p is 0, q is 1. The compound represented by the general formula (1) becomes the compound represented by the above general formula (2) having an episulfide group. On the other hand, when p is 1, q is 0. The compound represented by the general formula (1) becomes the compound represented by the above general formula (3) having a thietane group.

Concrete examples of the compound represented by the general formula (2) include tris(β-epithiopropylthio)phosphine, tris(β-epithiopropylthio)oxophosphorus(V), tris(β-epithiopropylthio)thiophosphorus(V), tris(β-epithiopropyl)phosphite, tris(β-epithiopropyl)phosphate, tris(β-epithiopropyl)thiophosphate and the like. However, the present invention is not restricted to these compounds.

Concrete examples of the compound represented by the general formula (3) include tris(3-thietanylthio)phosphine, tris(3-thietanylthio)oxophosphorus(V), tris(3-thietanylthio)thiophosphorus(V), tris(3-thietanyl)phosphite, tris(3-thietanyl)phosphate, tris(3-thietanyl)thiophosphate and the like. However, the present invention is not restricted to these compounds.

The compound represented by the general formula (2) of the present invention is typically produced by the reaction of a halide represented by the general formula (4) of P, P=O or P=S with a hydroxy compound or a thiol compound having an episulfide group represented by the general formula (5),

(4)

wherein, in the formula, M and Y are the same as those described above; Z represents a halogen atom; and p represents an integer of not less than 1 but not more than 3,

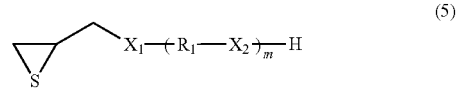

(5)

wherein, in the formula, $R_1$, $X_1$, $X_2$ and m are the same as those described above.

Furthermore, the compound represented by the general formula (3) of the present invention is typically produced by the reaction of a halide represented by the aforementioned general formula (4) of P, P=O or P=S with a hydroxy compound or a thiol compound having a thietane group represented by the general formula (6),

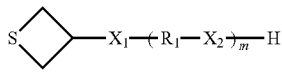

(6)

wherein, in the formula, $R_1$, $X_1$, $X_2$ and m are the same as those described above.

The compound represented by the general formula (4) is available as an industrial raw material or a research reagent. The compound represented by the general formula (5) is a known compound, and is produced in accordance with a method as described, for example, in SYNTHETIC COMMUNICATION, pp. 595 to 600 (2003). The compound represented by the general formula (6) is a known compound, and is produced in accordance with a method as described, for example, in Japanese Patent Laid-open No. 2003-327583.

The above reaction may be carried out without using a solvent or in the presence of an organic solvent which is inactive to the reaction.

Such an organic solvent is not particularly limited as long as it is inactive to the reaction. Examples thereof include hydrocarbon solvents such as petroleum ether, hexane, benzene, toluene, xylene, mesitylene and the like; ether solvents such as diethyl ether, tetrahydrofuran, diethylene glycol dimethyl ether and the like; ketone solvents such as acetone, methyl ethyl ketone, methyl isobutyl ketone and the like; ester solvents such as ethyl acetate, butyl acetate, amyl acetate and the like; chlorine-containing solvents such as methylene chloride, chloroform, chlorobenzene, dichlorobenzene and the like; and polar aprotic solvents such as N,N-dimethylformamide, N,N-dimethylacetamide, N,N-dimethylimidazolidinone, dimethyl sulfoxide and the like.

The reaction temperature is not particularly limited, but it is usually in the range of –78 to 200 degrees centigrade and preferably in the range of –78 to 100 degrees centigrade.

The reaction time is affected by the reaction temperature, but it is usually from several minutes to 100 hours.

In the above reaction, the amount of the compound represented by the general formula (4) and the compound represented by the general formula (5) is not particularly limited, but the amount of the compound represented by the general formula (5) used is usually not less than 0.01 and not more than 100 mole, based on 1 mole of the compound represented by the general formula (4). Furthermore, it is preferably not less than 0.1 and not more than 50 mole and more preferably not less than 0.5 and not more than 20 mole.

In addition, in the above reaction, the amount of the compound represented by the general formula (4) and the compound represented by the general formula (6) is not particularly limited, but the amount of the compound represented by the general formula (6) used is usually not less than 0.01 and not more than 100 mole, based on 1 mole of the compound represented by the general formula (4). Furthermore, it is preferably not less than 0.1 and not more than 50 mole and more preferably not less than 0.5 and not more than 20 mole.

The reaction may be carried out without using a catalyst or in the presence of a catalyst. In order to effectively carry out the reaction, it is preferable to employ a base. Examples of the base include pyridine, triethylamine, dimethylaniline, diethylaniline, 1,8-diazabicyclo[5,4,0]-7-undecene and the like.

The polymerizable composition of the present invention may contain a compound containing the compound represented by the general formula (1) as a polymerizable compound, and may further contain a polymerization catalyst.

At this time, the compound represented by the aforementioned general formula (1) may be used singly, or a plurality of different compounds represented by the general formula (1) may be used together. For example, the compound represented by the general formula (2) and the compound represented by the general formula (3) may be used in combination.

The amount of the compound represented by the general formula (1) used is not particularly limited, but it is usually not less than 10 weight %, preferably not less than 30 weight %, more preferably not less than 50 weight % and further preferably not less than 70 weight %, based on the total weight of the polymerizable compound contained in the polymerizable composition of the present invention.

The polymerization catalyst to be used for the polymerizable composition of the present invention is not particularly limited, and polymerization catalysts, known in the art as described, for example, in Japanese Patent Laid-Open No. 2003-327583 can be used. As the polymerization catalyst, there can be used, for example, an amine compound, a phosphine compound, an organic acid and its derivatives (salt, ester, acid anhydride or the like), an inorganic acid, an onium salt compound such as a quaternary ammonium salt compound, a quaternary phosphonium salt compound, a tertiary sulfonium salt compound, a secondary iodonium salt or the like, a Lewis acid compound, a radical polymerization catalyst, a cationic polymerization catalyst and the like.

The amount of the polymerization catalyst used is affected by the composition and polymerization conditions of the polymerizable composition, so it is not particularly limited. However, it is not less than 0.0001 and not more than 10 weight parts, preferably not less than 0.001 and not more than 5 weight parts, and more preferably not less than 0.005 and not more than 3 weight parts, based on 100 weight parts of the total polymerizable compound contained in the polymerizable composition.

The polymerizable composition of the present invention may further contain other polymerizable compounds in addition to the compound represented by the general formula (1) in the ranges in which the desired effect of the present invention is not impaired.

Examples of the polymerizable compound include various polymerizable monomers or polymerizable oligomers, known in the art. Examples thereof include a (meth) acrylic acid ester compound, a vinyl compound, an epoxy compound, an episulfide compound, an oxetane compound, a thietane compound and the like.

For example, the polymerizable composition of the present invention may further contain a compound represented by the following general formula (7) as another polymerizable compound,

(7)

The content of other polymerizable compounds is not particularly limited as long as the desired effect of the present invention is not impaired when contained, but it is usually not more than 90 weight %, preferably not more than 80 weight %, more preferably not more than 70 weight %, and further preferably not more than 50 weight %, based on the total weight of the polymerizable compound contained in the polymerizable composition of the present invention.

As a method for producing the polymerizable composition of the present invention, there can be typically exemplified a method involving using the compound represented by the general formula (1) of the present invention and various known polymerizable compounds as described above depending on the intended use together, adding the aforementioned polymerization catalyst, and then mixing and dissolving the resulting mixture. Furthermore, the polymerizable composition is preferably used for polymerization after it is thoroughly degassed under a reduced pressure as required and filtered off to remove insoluble substances, foreign substances or the like before polymerization.

Meanwhile, when the polymerizable composition is produced, various known additives can also be added in the ranges in which the effect of the present invention is not damaged, as desired. Examples of the additive include an internal mold release agent, a light stabilizer, an ultraviolet absorbent, an anti-oxidant, a coloring pigment (for example, cyanine green, cyanine blue and the like), a dye, a flowability regulator, a filler and the like.

The resin and the optical component composed of the resin of the present invention are obtained by polymerization of the aforementioned polymerizable composition. Such polymerization is suitably carried out according to various methods, known in the art from the past, used for producing plastic lenses. A typical method includes casting polymerization. Namely, the polymerizable composition of the present invention produced by the above method is degassed under a reduced pressure and filtered off using a filter as required, and then the polymerizable composition is injected into a mold and heated as required for carrying out polymerization. In this case, it is preferable to carry out polymerization by gradually heating from a low temperature to a high temperature.

The mold is composed of, for example, two pieces of mirror surface-ground molds via a gasket made of polyethylene, an ethylene vinyl acetate copolymer, polyvinyl chloride and the like. Typical examples of the mold include, though not restricted to, combined molds such as glass and glass, glass and plastic plate, glass and metal plate, and the like. The mold may be two pieces of molds fixed by a tape such as a polyester adhesive tape or the like. In addition, a known method such as the mold release process may be performed for the mold, as needed.

When carrying out casting polymerization, the polymerization temperature is affected by the polymerization conditions such as the kind of polymerization initiator and the like, so it is not particularly limited. But, it is usually from −50 to 200 degrees centigrade, preferably from −20 to 170 degrees centigrade and more preferably from 0 to 150 degrees centigrade.

The polymerization time is affected by the polymerization temperature, but it is usually from 0.01 to 100 hours and preferably from 0.05 to 50 hours. Polymerization can also be carried out in combination of several temperatures by conducting low temperature, temperature elevation, temperature dropping and the like as required.

Furthermore, the polymerizable composition of the present invention can also be polymerized by irradiation with an active energy ray such as electron beam, ultraviolet light, visible light or the like. At this time, a radical polymerization catalyst or a cationic polymerization catalyst for initiating polymerization by means of the active energy ray is used as required.

The thus-obtained resin and the lens composed of the resin may be used by forming a coating layer on one side or both sides if necessary. Examples of the coating layer include a primer layer, a hard coat layer, an anti-reflection layer, an anti-fog coating layer, an antifouling layer, a water-repellent layer and the like. These coating layers may be used singly, or a plurality of coating layers may be multi-layered and used. When the coating layers are formed on either side, the same coating layers or different coating layers may be formed on respective sides.

Known additives may be used to these coating layers together for the improvement in the performance of the lens. Concrete examples of the additive include ultraviolet absorbers for protecting lenses or eyes from ultraviolet rays; infrared ray absorbers for protecting eyes from infrared rays; light stabilizers or anti-oxidants for improving weather resistance of the lens; and dyes or pigments for enhancing fashionability of the lens. Further, a photochromic dye and a photochromic pigment, an anti-static agent or various other additives may be used. Furthermore, for the layer subjected to coating, various leveling agents may be used for the purpose of improving coatability.

A primer layer is usually formed between the hard coat layer to be described below and the optical lens. The primer layer is a coating layer for the purpose of enhancing adhesion between the hard coat layer to be formed thereon and the lens, and impact resistance can also be improved depending on the situation.

As the primer layer, any materials can be used as long as its adhesion to the obtained lens is high, but there can be usually used a urethane based resin, an epoxy based resin, a polyester based resin, a melanin based resin, a primer composition having polyvinylacetal as a main component and the like. A proper solvent which does not affect the lens may be used for the primer composition for purpose of adjusting the viscosity of the composition. Of course, a solvent may not be used.

The primer composition can be formed by either a coating method or a dry method. When the coating method is employed, a primer layer is formed by applying the primer composition in a known coating method such as spin coating or dip coating onto the lens and then solidifying the resultant. When the dry method is employed, a primer layer is formed by a known dry method such as CVD method or vacuum vapor deposition. In forming a primer layer, for the purpose of enhancing adhesion, the surface of the lens may be subjected to pre-treatment such as alkaline treatment, plasma treatment, ultraviolet ray treatment or the like as necessary.

A hard coat layer is a coating layer for the purpose of providing functions such as scratch resistance, abrasion resistance, moisture resistance, hot water resistance, heat resistance, weather resistance or the like to the lens surface.

As for the hard coat layer, there are generally used an organosilicon compound having curability, and a hard coating composition containing oxide particles containing one element selected from the element groups of Si, Al, Sn, Sb, Ta, Ce, La, Fe, Zn, W, Zr, In and Ti, and/or particles composed of composite oxide of two or more elements selected from these element groups. Oxide particles and/or particles composed of composite oxides may be used singly, or used in combination of two or more kinds for the hard coating composition. The hard coating composition preferably contains at least any one of amines, amino acids, metal-acetylacetonate complexes, organic acid metal salts, perchloric acids, salts of perchloric acids, acids, metal chlorides and polyfunctional epoxy compounds in addition to the above components. A proper solvent which does not affect the lens may be added to the hard coating composition. Of course, a solvent may be not be used.

The hard coat layer is usually formed by applying the hard coating composition in a known coating method such as spin coating or dip coating onto the lens and then curing. As the curing method, there can be exemplified heat curing, energy ray irradiation such as ultraviolet light, visible light or the like. In order to suppress occurrence of interference fringes, the difference between the refractive index of the hard coat layer and that of the lens is preferably in the range of ±0.1 (plus/minus).

An anti-reflection layer is usually formed on the aforementioned hard coat layer if necessary. There are inorganic and organic anti-reflection layers. In case of the inorganic type, the layer is formed by a dry method such as vacuum vapor deposition, sputtering method, ion plating method, ion beam assisted deposition method, CVD method and the like, using inorganic oxides such as $SiO_2$, $TiO_2$ and the like. In case of the organic type, it is formed by a wet method using an organosilicon compound and a composition containing silica-based fine particles having inner cavity.

The anti-reflection layer may be mono-layered and multi-layered. When it is mono-layered, the refractive index of the anti-reflection layer is preferably at least 0.1 or more lower than that of the hard coat layer. Furthermore, for effectively exhibiting anti-reflection functions, it is preferably a multi-layer anti-reflection layer. In that case, low refractive index layer and high refractive index layer are alternately laminated. Also, in this case, the difference between the refractive index of the low refractive index layer and that of the high refractive index layer is preferably not less than 0.1. As the high refractive index layer, layer of $ZnO$, $TiO_2$, $CeO_2$, $Sb_2O_5$, $SnO_2$, $ZrO_2$, $Ta_2O_5$ and the like can be cited, while as the low refractive index layer, layer of $SiO_2$ and the like can be cited.

On the anti-reflection layer, an anti-fog coating layer, an antifouling layer or a water-repellent layer may be formed, as required. As a method to form an anti-fog coating layer, an antifouling layer and a water-repellent layer, its treatment method and treatment materials are not particularly limited as long as anti-reflection functions are not adversely affected, and an anti-fog coating treatment method, an antifouling treatment method, a water-repellent treatment method and materials, known in the art, can be used.

For example, in the anti-fog coating method and antifouling treatment method, there can be exemplified a method involving covering the surface with a surfactant, a method involving adding a hydrophilic film to the surface to give water absorption, a method involving covering the surface with fine concavo-convex shapes to enhance water absorption, a method involving using photocatalytic activities to give water absorption, a method involving performing a super water-repellent treatment for preventing adhesion of a water droplet, and the like.

Furthermore, as the water-repellent treatment method, there can be exemplified a method involving using a fluorine-containing silane compound or the like for forming a water-repellent treatment layer by vapor deposition or sputtering, a method involving dissolving a fluorine-containing silane compound in a solvent and then coating for forming a water-repellent treatment layer, and the like.

Meanwhile, the thus-obtained resin and the lens composed of the resin may be dyed using a pigment according to the purpose in order to provide fashionability or photochromic property. Hereinafter, dyeing of an optical lens will be described.

An optical lens can be tinted according to a known tinting method, but it is usually dyed tinting by one of the following methods:

(a) a method involving dipping the lens into a tinting liquid;
(b) a method involving coating using a coating agent containing a colorant, or a method involving forming a tintable coating layer and tinting the coating layer;
(c) a method involving performing polymerization by containing a tintable material in a raw material monomer; and
(d) a method involving sublimating by heating a sublimation tinting.

The method (a) generally involves dipping a predetermined optical surface-finished lens cloth into a tinting liquid in which a pigment in use is dissolved or uniformly dispersed (tinting step) and then as necessary, heating the lens for solidifying the colorant (annealing step after tinting).

The colorant used for the tinting step is not particularly limited when it is, for example, a known colorant. But, an oil-soluble dye or a disperse dye is usually used. The solvent used for the tinting step is not particularly limited as long as the colorant in use can be dissolved or can be uniformly dispersed.

In this tinting step, a surfactant for dispersing the colorant in a tinting liquid or a carrier for promoting tinting may be added as necessary.

The tinting step involves preparing a dye bath by dispersing a colorant and a surfactant to be added as necessary in water or a mixture of water and an organic solvent, and dipping the optical lens in the dye bath for carrying out tinting at a prescribed temperature for a prescribed period of time. The dyeing temperature and time vary depending on the intended coloring concentration, but it is usually not more than 120 degrees centigrade for about several minutes to several tens of hours, while the dye concentration of the dye bath is from about 0.01 to 10 weight %. Furthermore, when it is difficult to dye, dyeing may be performed under pressure. The annealing step to be performed after tinting as necessary is a step of heating the dyed lens cloth. The heating treatment involves removing water remained on the surface of the lens cloth dyed in the tinting step with a solvent or drying the solvent, and then placing the resulting material, for example, in a furnace such as an infrared heating furnace, a resistance heating furnace or the like in an air atmosphere for a prescribed period of time. The annealing step after dyeing is to avoid decoloring of the dyed lens cloth (decoloring prevention treatment) and at the same time to remove water content penetrated into the lens cloth at the time of dyeing.

The method (b) is a method involving applying an organic coating solution obtained by dispersing or dissolving a colorant onto a plastic lens without directly tinting a plastic lens material and then curing for forming a tinted coating layer on the lens surface, or a method involving forming a tintable coating layer on the plastic lens surface and then adopting the method (a), that is, dipping the plastic lens in a tinting liquid and heating the resultant for tinting.

The method (c) is a method involving performing polymerization by previously dissolving a dye in a raw material monomer of a plastic lens. The colorant in use is not particularly limited as long as it can be uniformly dissolved in a raw material monomer or dispersed such that optical properties are not impaired.

As the method (d), the following (d1) to (d3) can be cited:

(d1) a method involving sublimating a solid sublimation colorant for tinting a plastic lens;
(d2) a method involving facing a substrate obtained by applying a solution containing a sublimation colorant to a plastic lens in a non-contact state, and heating the substrate and the lens for tinting; and
(d3) a method involving transferring a colored layer containing a sublimation colorant and a transfer layer composed of an adhesive layer onto a plastic lens and then heating the resultant for tinting.

The resin and the lens composed of the resin of the present invention may be tinted according to any of methods. The colorant in use is not particularly limited as long as it has a sublimation property.

Furthermore, for the resin cured product obtained by polymerizing the polymerizable composition of the present invention and optical components, transparency is high, heat resistance and mechanical strength are excellent, and the refractive index (nd) is high exceeding 1.7.

As the optical component of the present invention, there can be exemplified, various plastic lenses such as a spectacle lens for vision correction, a lens for cameras, a fresnel lens for liquid crystal projectors, a lenticular lens, a contact lens and the like; sealing materials for a light emitting diode (LED); optical waveguides; optical adhesive agents used for joining of an optical lens and an optical waveguide; anti-reflection films used for optical lenses and the like; and transparent coating or transparent substrates used for liquid crystal display device members (for example, a substrate, a light-guiding plate, a film, a sheet and the like).

The present invention further relates to a compound wherein, in the compound represented by the above general formula (1), n is 2 or 3. Such a compound can be included, for example, in the polymerizable composition of the present invention as a polymerizable compound.

EXAMPLES

The present invention is now more specifically illustrated below with reference to Production Examples and Examples. However, the present invention is not limited to these Examples.

Production of Compound Represented by the General Formula (2) of the Present Invention Reference Production Example 1

In accordance with a method as described in SYNTHETIC COMMUNICATION, pp. 595 to 600 (2003), 2,3-epithio-1-propanol was synthesized. Namely, 152 g of thiourea, 74 g of glycidol, 18.7 g of lithium tetrafluoroborate and 500 g of acetonitrile were introduced into a reactor equipped with a stirrer and a thermometer. The resulting material was stirred under reflux for 0.5 hours for carrying out the reaction. Thereafter, 300 g of water was added thereto and extracted twice each by using 500 g of chloroform. The obtained organic layer was dried over anhydrous sodium sulfate and then the solvent was removed using an evaporator. The resulting residue was purified by silica gel column chromatography to obtain 72 g of 2,3-epithio-1-propanol (isolated yield 80%).

Example A1

Production of Compound Represented by the Formula (2-1) of the Present Invention 42.6 g (0.473 mole) of 2,3-epithio-1-propanol was introduced to 500 g of dried tetrahydrofuran and the reaction solution was cooled down to −30 degrees centigrade. 50.1 g (0.495 mole) of dried triethylamine was added at the same temperature and the resulting mixture was stirred for 5 minutes. Subsequently, 90 ml of a tetrahydrofuran solution of thiophosphoryl chloride (corresponding to 0.150 mole of thiophosphoryl chloride) was introduced dropwise at −30 degrees centigrade for 2 hours. After the dropwise addition was completed, the solution was heated to −20 degrees centigrade and further stirred at the same temperature for 4 hours. This reaction mixture was filtered off for removing salt, and 600 ml of toluene and 600 ml of water were added thereto for separating an organic layer and a water layer. The organic layer was washed respectively with 500 ml of 1% $NaHCO_3$ aqueous solution and 500 ml of pure water two times, and then dried over anhydrous magnesium sulfate. Methylene dichloride and toluene were removed from this extract to obtain a crude composition. The resulting crude composition was purified by silica gel column chromatography with a development solvent of a mixed solution of hexane/toluene to obtain 21.5 g (yield 43%) of tris(β-epithiopropyl)thiophosphate of the following formula (2-1). 1H-NMR data is shown below (solvent: DMSO-d6, internal standard substance: TMS); δ2.50 (6H), δ3.10 (3H), δ3.50 (6H).

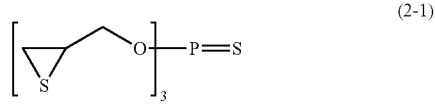

(2-1)

Example A2

Production of Compound Represented by the Formula (2-2) of the Present Invention 30.8 g (yield 54%) of tris(β-epithiopropylthio)thiophosphorus(V) of the following formula (2-2) was obtained in the same operation as in Example A1, except that 2,3-epithio-1-propanethiol was used instead of 2,3-epithio-1-propanol in Example A1. 1H-NMR data is shown below (solvent: $CDCl_3$, internal standard substance: TMS); δ2.35 (3H), δ2.65 (3H), δ3.10 (3H), δ3.25 (3H), δ3.45 (3H).

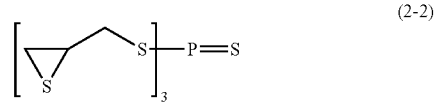

(2-2)

Example A3

Production of Compound Represented by the Formula (2-3) of the Present Invention 16.3 g (yield 30%) of tris(β-epithiopropylthio)oxophosphorus(V) of the following formula (2-3) was obtained in the same operation as in Example A1, except that 2,3-epithio-1-propanethiol was used instead of 2,3-epithio-1-propanol and phosphorus oxytrichloride was used instead of thiophosphoryl chloride in Example A1. 1H-NMR data is shown below (solvent: $CDCl_3$, internal standard substance: TMS); δ2.52 (6H), δ3.12 (3H), δ3.37 (6H).

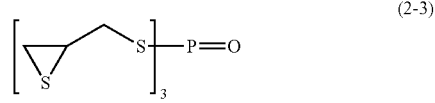

(2-3)

Example A4

Production of Compound Represented by the Formula (2-4) of the Present Invention 32.2 g (yield 62%) of tris(β-epithiopropylthio)phosphine of the following formula (2-4) was obtained in the same operation as in Example A1, except that 2,3-epithio-1-propanethiol was used instead of 2,3-epithio-1-propanol and phosphorus trichloride was used instead of thiophosphoryl chloride in Example A1. 1H-NMR data is shown below (solvent: CDCl₃, internal standard substance: TMS); δ2.46 (6H), δ3.00 (3H), δ3.33 (6H).

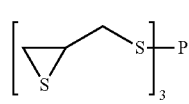

(2-4)

<Preparation of Polymerizable Composition and Production of Resin Cured Product by Polymerization of the Composition>

The physical properties of the resins or optical components (lenses) produced in the following Examples were evaluated in the following methods.

Appearance: The color tone, transparency and existence of optical distortion were confirmed visually or using a microscope.

Refractive index: It was measured at 20 degrees centigrade using a Pulfrich refractometer.

Drop ball test: A steel ball was free-falling on a lens from a height of 127 cm for carrying out a test to observe whether the lens having a central thickness of 1 mm was broken or not.

Example A5

At room temperature (25 degrees centigrade), 30 g of the compound represented by the formula (2-1) produced in Example A1 was weighed in a glass beaker, and 0.15 g of trifluoromethanesulfonic acid was added as a polymerization catalyst. Thereafter, the resulting solution was stirred and fully mixed. The obtained mixed solution was filtered off using a Teflon (registered trademark) filter and then thoroughly degassed under a reduced pressure of not more than 1.3 kPa until no bubble was observed. The polymerizable composition was injected into a mold composed of a glass mold and a tape. Then, the resultant was put into a heating oven and then gradually heated from 30 to 120 degrees centigrade to perform polymerization for 20 hours.

A molded piece of the obtained resin was excellent in transparency and its appearance was good without any distortion. The refractive index of the obtained resin was measured and as a result, the refractive index nd was 1.732. The test piece was not broken at the drop ball test with a ball of 12 g.

Example A6

A test was conducted in the same manner as in Example A5, except that the compound represented by the formula (2-2) produced in Example A2 was used instead of the compound represented by the formula (2-1) in Example A5.

A molded piece of the obtained resin was excellent in transparency and its appearance was good without any distortion. The refractive index of the obtained resin was measured and as a result, the refractive index nd was 1.760. The test piece was not broken at the drop ball test with a ball of 12 g.

Example A7

A test was conducted in the same manner as in Example A5, except that the compound represented by the formula (2-3) produced in Example A3 was used instead of the compound represented by the formula (2-1) in Example A5.

A molded piece of the obtained resin was excellent in transparency and its appearance was good without any distortion. The refractive index of the obtained resin was measured and as a result, the refractive index nd was 1.728. The test piece was not broken at the drop ball test with a ball of 12 g.

Example A8

A test was conducted in the same manner as in Example A5, except that the compound represented by the formula (2-4) produced in Example A4 was used instead of the compound represented by the formula (2-1) in Example A5.

A molded piece of the obtained resin was excellent in transparency and its appearance was good without any distortion. The refractive index of the obtained resin was measured and as a result, the refractive index nd was 1.737. The test piece was not broken at the drop ball test with a ball of 12 g.

Production of Compound Represented by the General Formula (3) of the Present Invention Reference Production Example 2

In accordance with a method as described in Japanese Patent Laid-open No. 2003-327583, 3-mercaptothietane was synthesized. Namely, 190 g of thiourea, 253 g of 35% hydrochloric acid solution and 250 g of water were introduced into a reactor equipped with a stirrer and a thermometer, and stirred. To the reaction solution was added dropwise 156 g of 3-thiethanol for 1 hour. The resulting solution was stirred and reacted at 30 degrees centigrade for 24 hours, and then 177 g of 24% ammonia water was added dropwise thereto for 1 hour. The solution was further reacted at 30 degrees centigrade for 15 hours and then allowed to stand for taking out an organic layer (under layer) to obtain 134 g of a crude composition. The resulting crude composition was distilled under a reduced pressure to collect a fraction with a boiling point of 40 degrees centigrade/106 Pa to obtain a desired product of a colorless transparent liquid, i.e., 3-mercaptothietane.

Example B1

Production of Compound Represented by the Formula (3-1) of the Present Invention 42.6 g (0.473 mole) of 3-thiethanol was introduced to 500 g of dried tetrahydrofuran and the reaction solution was cooled down to −30 degrees centigrade. 50.1 g (0.495 mole) of dried triethylamine was added at the same temperature and the resulting mixture was stirred for 5 minutes. Subsequently, 90 ml of a tetrahydrofuran solution of thiophosphoryl chloride (corresponding to 0.150 mole of thiophosphoryl chloride) was introduced dropwise at −30 degrees centigrade for 2 hours. After the dropwise addition was completed, the solution was heated to −20 degrees centigrade and further stirred at the same temperature for 4 hours. This reaction mixture was filtered off for removing salt, and 600 ml of toluene and 600 ml of water were added thereto for separating an organic layer and a water layer. The organic layer was washed respectively with 500 ml of 1% NaHCO₃ aqueous solution and 500 ml of pure water two times, and then dried over anhydrous magnesium sulfate. Methylene dichloride and toluene were removed from this extract to obtain a crude composition. The resulting crude composition was purified by silica gel column chromatography with a development solvent of a mixed solution of hexane/toluene to obtain 21.5 g (yield 43%) of tris(3-thietanyl)thiophosphate of the following formula (3-1). 1H-NMR data is shown below (solvent: DMSO-d6, internal standard substance: TMS); δ3.30 (12H), δ5.12 (3H).

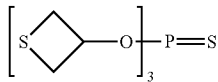
(3-1)

Example B2

Production of Compound Represented by the Formula (3-2) of the Present Invention 30.8 g (yield 54%) of tris(3-thietanylthio)thiophosphorus (V) of the following formula (3-2) was obtained in the same operation as in Example B1, except that 3-mercaptothietane was used instead of 3-thiethanol in Example B1. 1H-NMR data is shown below (solvent: CDCl₃, internal standard substance: TMS); δ3.35 (6H), δ3.61 (6H), δ4.92 (3H).

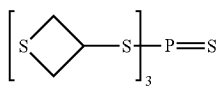
(3-2)

Example B3

Production of Compound Represented by the Formula (3-3) of the Present Invention 16.3 g (yield 30%) of tris(3-thietanylthio)oxophosphorus (V) of the following formula (3-3) was obtained in the same operation as in Example B1, except that 3-mercaptothietane was used instead of 3-thiethanol and phosphorus oxytrichloride was used instead of thiophosphoryl chloride in Example B1. 1H-NMR data is shown below (solvent: CDCl₃, internal standard substance: TMS); δ3.35 (6H), δ3.65 (6H), δ4.92 (3H).

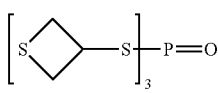
(3-3)

Example B4

Production of Compound Represented by the Formula (3-4) of the Present Invention 32.2 g (yield 62%) of tris(3-thietanylthio)phosphine of the following formula (3-4) was obtained in the same operation as in Example B1, except that 3-mercaptothietane was used instead of 3-thiethanol and phosphorus trichloride was used instead of thiophosphoryl chloride in Example B1. 1H-NMR data is shown below (solvent: CDCl₃, internal standard substance: TMS); δ3.25 (6H), δ3.62 (6H), δ4.70 (3H).

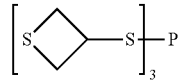
(3-4)

<Preparation of Polymerizable Composition and Production of Resin Cured Product by Polymerization of the Composition>

The physical properties (appearance, refractive index, falling ball test) of the resins or optical components (lenses) produced in the following Examples were evaluated in the same methods as described above.

Example B5

At room temperature (25 degrees centigrade), 30 g of the compound represented by the formula (3-1) produced in Example B1 was weighed in a glass beaker, and 0.15 g of trifluoromethanesulfonic acid was added as a polymerization catalyst. Thereafter, the resulting solution was stirred and fully mixed. The obtained mixed solution was filtered off using a Teflon (registered trademark) filter and then thoroughly degassed under a reduced pressure of not more than 1.3 kPa until no bubble was observed. The polymerizable composition was injected into a mold composed of a glass mold and a tape. Then, the resultant was put into a heating oven, and then gradually heated from 30 to 120 degrees centigrade to perform polymerization for 20 hours.

A molded piece of the obtained resin was excellent in transparency and its appearance was good without any distortion. The refractive index of the obtained resin was measured and as a result, the refractive index nd was 1.737. The specific gravity was 1.49 and the test piece was not broken at the drop ball test with a ball of 12 g.

Example B6

A test was conducted in the same manner as in Example B5, except that the compound represented by the formula (3-2) produced in Example B2 was used instead of the compound represented by the formula (3-1) in Example B5.

A molded piece of the obtained resin was excellent in transparency and its appearance was good without any distortion. The refractive index of the obtained resin was measured and as a result, the refractive index nd was 1.767. The specific gravity was 1.51 and the test piece was not broken at the drop ball test with a ball of 12 g.

Example B7

A test was conducted in the same manner as in Example B5, except that the compound represented by the formula (3-3) produced in Example B3 was used instead of the compound represented by the formula (3-1) in Example B5.

A molded piece of the obtained resin was excellent in transparency and its appearance was good without any distortion. The refractive index of the obtained resin was measured and as a result, the refractive index nd was 1.733. The specific gravity was 1.50 and the test piece was not broken at the drop ball test with a ball of 12 g.

Example B8

A test was conducted in the same manner as in Example B5, except that the compound represented by the formula (3-4) produced in Example B4 was used instead of the compound represented by the formula (3-1) in Example B5.

A molded piece of the obtained resin was excellent in transparency and its appearance was good without any distortion. The refractive index of the obtained resin was measured and as a result, the refractive index nd was 1.743. The specific gravity was 1.49.

Comparative Example 1

5 g of benzylamine was dissolved in 100 g of bis(2,3-epithiopropyl) disulfide. Next, 0.2 g of N,N-dicyclohexylmethylamine was added as a curing catalyst and mixed. This monomer mixture was degassed at a degree of vacuum of 1,330 Pa for 0.5 hours and then injected into a mold composed of a glass mold and a gasket. The resultant was put into a heating oven and gradually heated from 30 to 120 degrees centigrade to perform polymerization for 20 hours.

A molded piece of the obtained resin was excellent in transparency and its appearance was good without any distortion. The refractive index of the obtained resin was measured and as a result, the refractive index nd was 1.730. The test piece was broken at the drop ball test with a ball of 8 g.

Comparative Example 2

5 g of benzylamine was dissolved in 100 g of bis(2,3-epithiopropyl) sulfide. Next, 0.2 g of N,N-dicyclohexylmethylamine was added as a curing catalyst and mixed. This monomer mixture was degassed at a degree of vacuum of 1,330 Pa for 0.5 hours and then injected into a mold composed of a glass mold and a gasket. The resultant was put into a heating oven and gradually heated from 30 to 120 degrees centigrade to perform polymerization for 20 hours.

A molded piece of the obtained resin was excellent in transparency and its appearance was good without any distortion. The refractive index of the obtained resin was measured and as a result, the refractive index nd was 1.706. The test piece was broken at the drop ball test with a ball of 8 g.

Reference Production Example 3

11.15 g (0.105 mole) of 3-mercaptothietane was introduced to 50 g of pure water, and subsequently 41.2 g of a 10% NaOH aqueous solution (0.103 mole) was introduced dropwise at room temperature for 40 minutes. Then, the reaction solution was heated to 30 degrees centigrade and 65.2 g (corresponding to 0.025 mole of tin tetrachloride) of an aqueous solution of 10% tin tetrachloride was introduced dropwise at the same temperature for 4 hours. After the dropwise addition was completed, the solution was further stirred at the same temperature for 2 hours. 100 ml of chloroform was added to the reaction mixture for separating an organic layer and a water layer. The organic layer was washed with 100 ml of pure water two times and then dried over anhydrous sodium sulfate. The solvent was removed from this extract to obtain 13.40 g (yield 99%) of a compound represented by the formula (7),

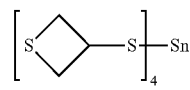

(7)

Example B9

At 40 degrees centigrade, 27 g of the compound represented by the formula (3-2) produced in Example B2 and 3 g of the compound represented by the above formula (7) were weighed in a glass beaker. The resulting solution was stirred and fully mixed without adding a polymerization catalyst. The obtained mixed solution was filtered off using a Teflon (registered trademark) filter and then thoroughly degassed under a reduced pressure of not more than 1.3 kPa until no bubble was observed. The polymerizable composition was injected into a mold composed of a glass mold and a tape. Then, the resultant was put into a heating oven and gradually heated from 60 to 120 degrees centigrade to perform polymerization for 20 hours.

A molded piece of the obtained resin was excellent in transparency and its appearance was good without any distortion. The refractive index of the obtained resin was measured and as a result, the refractive index nd was 1.771. The specific gravity was 1.60 and the test piece was not broken at the drop ball test with a ball of 12 g.

Comparative Example 3

At room temperature (25 degrees centigrade), 36.4 g of m-xylylene diisocyanate, 0.0105 g of di-n-butyltin dichloride, 0.070 g of an internal mold release agent (product name: Zelec UN manufactured by STEPAN Company) and 0.035 g of an ultraviolet absorber (product name: BioSorb 583 manufactured by Kyodo Chemical Co., Ltd.) were mixed and dissolved in a glass beaker at 20 degrees centigrade to give a uniform solution. 33.6 g of 4-mercaptomethyl-1,8-dimercapto-3,6-dithiaoctane was added to the uniform solution, mixed and dissolved. This mixed solution was degassed at 400 Pa for 1 hour, filtered off using a Teflon (registered trademark) filter, and injected into a mold composed of a glass mold and a tape. Thereafter, the resultant was gradually heated from 25 to 120 degrees centigrade for 21 hours to perform polymerization.

A molded piece of the obtained resin was excellent in transparency and its appearance was good without any distortion. The refractive index of the obtained resin was measured and as a result, the refractive index nd was 1.660. Further, the test piece was not broken at the falling ball test with a ball of 12 g.

The invention claimed is:

1. A polymerizable composition containing a compound represented by the following general formula (1),

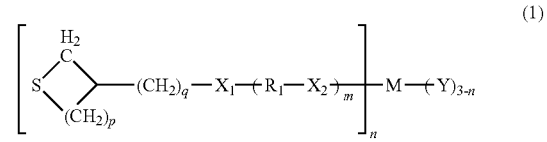

(1)

wherein, in the formula, M represents P, P=O or P=S; $X_1$ represents a sulfur atom or an oxygen atom; m represents 0; n represents 2 or 3; p and q represent (1, 0) or (0, 1); and Y represents an inorganic or organic residue.

2. The polymerizable composition as set forth in claim 1, wherein said general formula (1) is represented by the following general formula (2),

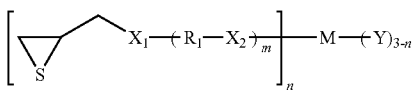
(2)

wherein, in the formula, M represents P, P=O or P=S; $X_1$ represents a sulfur atom or an oxygen atom; m represents 0; n represents 2 or 3; and Y represents an inorganic or organic residue.

3. The polymerizable composition as set forth in claim 2, wherein, in said compound represented by the general formula (2), $X_1$ is a sulfur atom.

4. The polymerizable composition as set forth in claim 2, wherein, in said compound represented by the general formula (2), n is 3 and $X_1$ is a sulfur atom.

5. The polymerizable composition as set forth in claim 1, wherein said general formula (1) is represented by the following general formula (3),

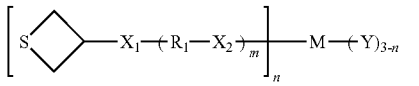
(3)

wherein, in the formula, M represents P, P=O or P=S; $X_1$ represents a sulfur atom or an oxygen atom; m represents 0; n represents 2 or 3; and Y represents an inorganic or organic residue.

6. The polymerizable composition as set forth in claim 5, wherein, in said compound represented by the general formula (3), $X_1$ is a sulfur atom.

7. The polymerizable composition as set forth in claim 5, wherein, in said compound represented by the general formula (3), n is 3 and $X_1$ is a sulfur atom.

8. The polymerizable composition as set forth in claim 1, further containing a compound represented by the following general formula (7),

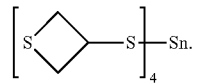
(7)

9. A method for producing a resin comprising a step of subjecting the polymerizable composition as set forth in claim 1 to casting polymerization.

10. A resin obtained by polymerization of the polymerizable composition as set forth in claim 1.

11. An optical component comprising the resin as set forth in claim 10.

12. A lens comprising the resin as set forth in claim 10.

13. A method for producing a resin comprising a step of subjecting the polymerizable composition as set forth in claim 2 to casting polymerization.

14. A method for producing a resin comprising a step of subjecting the polymerizable composition as set forth in claim 5 to casting polymerization.

15. A method for producing a resin comprising a step of subjecting the polymerizable composition as set forth in claim 8 to casting polymerization.

16. A resin obtained by polymerization of the polymerizable composition as set forth in claim 2.

17. A resin obtained by polymerization of the polymerizable composition as set forth in claim 5.

18. A resin obtained by polymerization of the polymerizable composition as set forth in claim 8.

* * * * *